US00PP23429P2

(12) United States Plant Patent
Parham

(10) Patent No.: US PP23,429 P2
(45) Date of Patent: Feb. 26, 2013

(54) ***CHRYSANTHEMUM* PLANT NAMED 'FOXY TIME YELLOW IMPROVED'**

(50) Latin Name: *Chrysanthemum morifolium*
Varietal Denomination: Foxy Time Yellow Improved

(75) Inventor: Ruth Parham, Bognor Regis (GB)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 0 days.

(21) Appl. No.: 13/136,008

(22) Filed: Jul. 20, 2011

Related U.S. Application Data

(60) Provisional application No. 61/404,509, filed on Oct. 5, 2010.

(51) Int. Cl.
*A01H 5/00* (2006.01)

(52) U.S. Cl. ..... Plt./295

(58) Field of Classification Search ..... Plt./295
See application file for complete search history.

(56) References Cited

U.S. PATENT DOCUMENTS

PP21,366 P2 10/2010 Parham

OTHER PUBLICATIONS

2004 Ficor Catalog listing *Chrysanthemum* variety 'Saffron Time' at p. 5 and a color photo at p. 13.

*Primary Examiner* — Kent L Bell
(74) *Attorney, Agent, or Firm* — Phase M, LLP

(57) ABSTRACT

A new variety of *Chrysanthemum* plant named 'Foxy Time Yellow Improved', having bright yellow spoon tip anemone inflorescences with a slightly green centre. The plants have a tidy compact habit with good foliage.

1 Drawing Sheet

Latin name of the genus and species: Botanical classification: *Chrysanthemum morifolium.*

Variety denomination: The new *Chrysanthemum* variety denomination is 'Foxy Time Yellow Improved'.

BACKGROUND OF THE INVENTION

The present invention comprises a new and distinct cultivar of *Chrysanthemum* botanically known as *Chrysanthemum morifolium*, and referred to by the cultivar name 'Foxy Time Yellow Improved'.

'Foxy Time Yellow Improved', identified as 22824-2 was discovered as a naturally occurring whole plant mutation in a controlled cultivated planting of the variety 'Foxy Time' (U.S. Plant Pat. No. 21,366).

The new variety 'Foxy Time Yellow Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Foxy Time Yellow Improved' is a pot type of *Chrysanthemum* plant variety having bright yellow spoon tip anemone inflorescences with a slightly green centre.

COMPARISON WITH PARENT CULTIVAR

Plants of the new *Chrysanthemum* variety 'Foxy Time Yellow Improved' are similar to the parent cultivar 'Foxy Time' in plant habit and growth rate. In side-by-side comparisons in Chichester, West Sussex, United Kingdom, under commercial practice, plants of the new *Chrysanthemum* variety 'Foxy Time Yellow Improved' differed from plants of the parent cultivar 'Foxy Time' in the following characteristics:

1. The new variety 'Foxy Time Yellow Improved' produces yellow spoon tipped anemone inflorescences whereas the parent cultivar 'Foxy Time' produces golden yellow spoon tips with blushed orange red quill anemone inflorescences.

COMPARISON WITH 'SAFFRON TIME'

Plants of the new *Chrysanthemum* variety 'Foxy Time Yellow Improved' are similar to plants of the unpatented variety 'Saffron Time', in plant habit and growth rate. However, in side-by-side comparisons in Chichester, West Sussex, United Kingdom, under commercial practice, plants of the new *Chrysanthemum* variety 'Foxy Time Yellow Improved' differed from plants of 'Saffron Time' in the following characteristics:

1. The new variety 'Foxy Time Yellow Improved' produces yellow anemone inflorescences with spoon tips whereas 'Saffron Time' produces yellow anemone inflorescences with elongated oblong shaped ray florets.
2. Plants of the new variety 'Foxy Time Yellow Improved' have larger inflorescences than plants of 'Saffron Time'.
3. Plants of the new variety 'Foxy Time Yellow Improved' have shorter response time than plants of 'Saffron Time'.

BRIEF DESCRIPTION OF ILLUSTRATIONS

Typical specimens of the plant and inflorescences for the new *Chrysanthemum* variety 'Foxy Time Yellow Improved' are shown in the accompanying digital photograph. The colors shown are as true as possible within the usual limits of this kind of illustration.

FIG. 1 is a whole plant view of the new variety 'Foxy Time Yellow Improved' grown in a pot. The plant shown in the illustration and described below is 54 days from the onset of Short Days.

DETAILED BOTANICAL DESCRIPTION

The following description of the new *Chrysanthemum* variety 'Foxy Time Yellow Improved' is of plants grown in a greenhouse in Chichester, West Sussex, United Kingdom, in the month of July. The cultivar has not been observed under all possible environmental conditions. The phenotype may vary significantly with variations in the environment such as temperature, length of day and light intensity, without any variance in genotype. The commercial classification of the new variety is a Pot *Chrysanthemum.*

Plants of the new variety have been grown successfully under temperature conditions averaging about 18° C. at night and about 24° C. to 25° C. during the day under assimilated light conditions of about 2500 lux. The plants respond well to the use of growth retardant, such as 3-4 applications of B9 with an average dosage of about 2 gram per liter. To produce a commercial product, the plants may be pinched once with the center bud removed. The typical container size for commercial growth is 1 liter. It has been observed that the shelf life of the new variety is about 28 days with a response time of about 7½ weeks. The new variety is suitable for growth in a temperature range of about 15° C. to 25° C.

The following description is with respect to a plant produced as pot *Chrysanthemum*. In the description of this new *Chrysanthemum* variety, color values have been taken from The Royal Horticultural Society Colour Chart (R.H.S.C.C.) by comparison to the new *Chrysanthemum* variety itself and may differ from the colors shown in the accompanying photograph.

PLANT

Plant type: Pot.
Habit: Upright and free branching.
Height (cm): 15.
Width (cm): 24.
Stem:
- *Length* (*cm*).—4.
- *Diameter* (*cm*).—0.4.
- *Texture*.—Slightly pubescent.
- *Color.*—138B.

Branching characteristics: Upright and free branching.
Lateral branches:
- *Length* (*cm*).—9.
- *Diameter* (*cm*).—0.2.
- *Texture*.—Slightly pubescent.

Number of breaks from pinch: 5.
Response time: 52 days.
Vigor: Medium.
Shelf life: 28 days.
Life of blooms: 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of about 2 gm/liter B9 @ 2, 21 and 28 days after sticking unrooted cuttings. The plants were grown for two weeks in Long Day conditions (20 hours of light) and then transferred to Short Day conditions (13 hours of dark).
Propagation:
- *Type*.—Vegetative propagation via stem cuttings.
- *Time to rooting.*—14 days with soil temperatures of 18° C.
- *Rooting habit*.—After 7 Long Days, the first roots emerge and form root primordia. After 14 Long Days, a complete root system is developed.

FOLIAGE

Number of leaves per lateral branch: 9.
Compound or single: Single.
Arrangement of leaves: Alternate.
- *Shape of leaf.*—Typically 5 lobed.
- *Size of leaf.*—Width (cm): 5 Length (cm): 8.
- *Leaf apex*.—Acute.
- *Base*.—Obtuse.
- *Attachment*.—Petioled.
- *Aspect*.—Slightly undulating.
- *Margin*.—Palmately lobed.
- *Surface characteristics*.—Top: Slightly pubescent. Bottom: Pubescent.

Petiole:
- *Color*.—Near 137C.
- *Length* (*cm*).—1.8.
- *Diameter* (*cm*).—0.3.
- *Surface*.—Slightly pubescent.

Venation: Net, prominent lateral and mid-veins at underside.
- *Color*.—Upper side: slightly lighter than 138B under side: 138B.

Color:
- *Mature leaf, upper side.*—138A; under side: 139C.
- *Young leaf, upper side.*—137A; under side: 139C.

INFLORESCENCE

Inflorescence appearance: Matte.
Inflorescence type: Anemone.
Inflorescence form: Slightly cupped.
Inflorescence shape: Circular.
Florescence habit: Domed.
Number of blossoms per branch: 4.
Typical and observed florescence season: January to December.
Inflorescence form: Cyme.
- *Depth of fully expanded blossoms* (*cm*).—1.8.
- *Diameter of fully expanded blossoms* (*cm*).—6.5.
- *Anemone center diameter* (*cm*).—2.5.

Phyllaries:
- *Number.*—24.
- *Color.*—137D.
- *Length* (*cm*).—0.5 to 0.8.
- *Width* (*cm*).—0.1 to 0.3.
- *Texture/appearance*.—Pubescent.
- *Shape*.—Elliptic.
- *Apex*.—Acute.
- *Margin*.—Entire.

Peduncle:
- *Length* (*cm*).—9.
- *Diameter* (*cm*).—0.2.
- *Angle from stem* (*degrees*).—40.
- *Color.*—138B.
- *Surface*.—Slightly pubescent.
- *Habit*.—Slightly undulating.
- *Strength*.—Medium.

Pedicel:
*Length*.—Terminal (cm): 3.5 lateral (cm): 4.
*Diameter* (*cm*): 0.2.
*Color*.—138B.
*Angle from the stem* (*degrees*).—40.
*Surface*.—Slightly pubescent.
*Habit*.—Slightly undulating.
*Strength*.—Medium.
Ray florets:
*Form/shape*.—Cylindrical with spoon tips.
*Texture/appearance*.—Matte.
*Number per inflorescence*.—52.
Quill:
*Length* (*cm*).—3 Width (cm): 0.4 tapers to 0.1.
Spoon:
*Length* (*cm*).—0.3 to 1.2 Width (cm): 0.4 to 0.7.
*Apex*.—Rounded.
*Base*.—Tapered.
*Margin*.—Entire.
Disc florets:
*Form/shape*.—Cylindric.
*Texture/appearance*.—Matte.
*Number per inflorescence*.—More than 200.
*Length* (*cm*).—1.3; Width (cm): 0.2.
*Diameter of disc* (*cm*).—3.2.
Fragrance: None.
Inflorescence bud (at onset of color):
*Length* (*cm*).—1.
*Diameter* (*cm*).—1.
*Form/shape*.—Round.
General inflorescence color:
1. *Ray florets, upper side*.—Immature: Spoon tips: 6A. Tube: 6C. Mature: Spoon tips: 6A. Tube: 6C. Older/Fading: Spoon tips: 6A. Tube: 6C.
2. *Ray florets, under side*.—Immature: Spoon tip and tube: 6C. Mature: 6C. Older/Fading: 6C.
3. *Ray florets, tube*.—Outer side: 6C.
4. *Ray florets, tube*.—Inner side: 6A.
5. *Disc florets*.—Immature: 7A, and 143A. Mature: 7A, with a hint of 154A. Older/Fading: 7A and a fading hint of 154A.
6. *Bud* (*at onset of color*).—7A.

Inflorescence progression with age: There is no difference in inflorescence form or colour change with age.

REPRODUCTIVE ORGANS

Gynoecium present on Ray and Disc florets.
Ray florets per individual inflorescence: Pistillate.
*Pistil number*.—52.
*Stigma color*.—154A.
*Stigma shape*.—Forked.
*Style color*.—154B.
*Style length* (*cm*).—0.5.
Disc florets per individual inflorescence: Pistillate.
*Pistil number*.—More than 200.
*Stigma color*.—154A.
*Stigma shape*.—Forked.
*Style color*.—154B.
*Style length* (*cm*).—0.5.
Androecium present on disc florets: Staminate.
*Stamen number*.—200 approx.
*Anther shape*.—Thread.
*Anther color*.—12A.
*Pollen color*.—14A.
*Pollen quantity*.—Plenty.
Fruit and seeds: None observed.

What is claimed is:

1. A new and distinct variety of *Chrysanthemum* plant, substantially as described and illustrated herein.

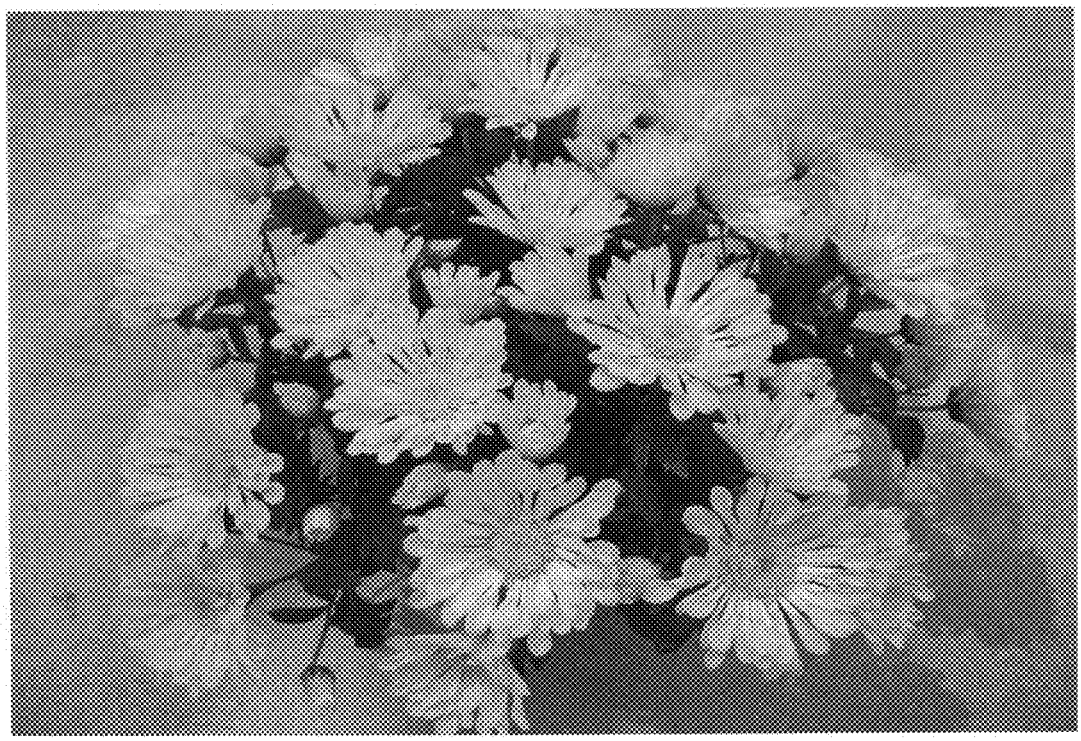

* * * * *